United States Patent
Tsuchida et al.

(10) Patent No.: US 7,863,473 B2
(45) Date of Patent: Jan. 4, 2011

(54) METHOD OF PRODUCING ORGANOSILYLAMINE CONTAINING RADIATION-POLYMERIZABLE FUNCTIONAL GROUP AND ORGANOSILYLAMINE CONTAINING RADIATION-POLYMERIZABLE FUNCTIONAL GROUP

(75) Inventors: Kazuhiro Tsuchida, Takasaki (JP); Masaaki Yamaya, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/194,632

(22) Filed: Aug. 20, 2008

(65) Prior Publication Data
US 2009/0054673 A1 Feb. 26, 2009

(30) Foreign Application Priority Data
Aug. 21, 2007 (JP) ............................. 2007-214643

(51) Int. Cl.
*C07F 7/10* (2006.01)
(52) U.S. Cl. ........................... 556/410; 522/10; 522/22
(58) Field of Classification Search ....................... None
See application file for complete search history.

(56) References Cited

U.S. PATENT DOCUMENTS

| | | | |
|---|---|---|---|
| 3,481,964 A | 12/1969 | Ismail et al. | |
| 3,927,057 A | 12/1975 | Takamizawa et al. | |
| 4,617,078 A | 10/1986 | Takahashi et al. | |
| 5,117,027 A * | 5/1992 | Bernhardt et al. | ........... 556/440 |
| 5,874,602 A * | 2/1999 | Manzouji et al. | ........... 556/463 |

FOREIGN PATENT DOCUMENTS

| | | |
|---|---|---|
| EP | 0 483 480 A1 | 5/1992 |
| WO | WO 2007/050580 A2 | 5/2007 |

* cited by examiner

*Primary Examiner*—Daniel M Sullivan
*Assistant Examiner*—Yevegeny Valenrod
(74) *Attorney, Agent, or Firm*—Oblon, Spivak, McClelland, Maier & Neustadt, L.L.P.

(57) ABSTRACT

A method of producing an organosilylamine containing a radiation-polymerizable functional group that is useful as a surface treatment agent is provided. The method includes reacting an organosilylamine containing a haloalkyl group, and at least one salt having a radiation-polymerizable functional group selected from the group consisting of alkali metal salts of organic acids having a radiation-polymerizable functional group and alkaline earth metal salts of organic acids having a radiation-polymerizable functional group, at a temperature within a range from 50 to 150° C. An organosilylamine containing a radiation-polymerizable functional group composed of a specific silazane unit is also provided.

11 Claims, 4 Drawing Sheets

METHOD OF PRODUCING ORGANOSILYLAMINE CONTAINING RADIATION-POLYMERIZABLE FUNCTIONAL GROUP AND ORGANOSILYLAMINE CONTAINING RADIATION-POLYMERIZABLE FUNCTIONAL GROUP

BACKGROUND OF THE INVENTION

1. Field of the Invention

The present invention relates to a novel method of producing an organosilylamine, and also relates to a novel organosilylamine. More specifically, the present invention relates to a novel method of producing an organosilylamine that contains a radiation-polymerizable functional group within the molecule, and also relates to a novel organosilylamine containing a radiation-polymerizable functional group within the molecule.

2. Description of the Prior Art

In an organosilylamine, the silicon-nitrogen bond contained within the molecule generally undergoes a deammonization reaction in the presence of water or a hydroxyl group to form a silicon-oxygen bond, and as a result, organosilylamines are widely used as silyl blocking agents for hydroxyl groups and the like, and as surface treatment agents and the like for inorganic oxides and inorganic substrates.

However, in almost all of the organosilylamines used for the above purposes, the organic functional group bonded to the silicon atom is a simple hydrocarbon-based organic functional group such as an alkyl group or a vinyl group, and very few organosilylamines are known in which other organic functional groups, including organic functional groups having polymerization reactivity such as radiation-polymerizability, are bonded to the silicon atom.

Although being typical compounds, organosilylamines are restricted in terms of the organic functional groups that can be introduced into the molecule, and therefore methods of producing the organosilylamines are also restricted. In other words, conventionally, a production method is used in which the organosilylamine is produced by a dehydrohalogenation reaction of the corresponding organohalosilane with ammonia, a primary amine or a secondary amine (see Patent References 1 to 3). However, with this method, synthesis of an organosilylamine having a functional group that exhibits favorable reactivity with amines is problematic. Furthermore, in the above method, the ammonia, primary amine or secondary amine that is used as a raw material, and ammonia in particular, has a high degree of toxicity and must be handled with considerable caution. Moreover, in the above reaction, following completion of the dehydrohalogenation reaction, by-products such as hydrogen halides and ammonium halides or hydrohalides of the primary amine or secondary amine, as well as residual ammonia, must be removed from the reaction system, and this process is complex. In other words, conventional methods of production could be improved in terms of productivity and safety.

It has been postulated that organosilylamines having a radiation (UV radiation) polymerizable group such as a methacryloyl group or acryloyl group as an organic functional group should enable the ready introduction of radiation-polymerizable groups at the terminals or surfaces of inorganic oxides such as silicone or silica, or at the surfaces of inorganic substrates, and as such, could be described as long-awaited surface treatment agents.

[Patent Reference 1] U.S. Pat. No. 3,927,057
[Patent Reference 2] U.S. Pat. No. 3,481,964
[Patent Reference 3] U.S. Pat. No. 4,617,078

SUMMARY OF THE INVENTION

The present invention has been designed in light of the above circumstances, and has an object of providing a novel method of producing an organosilylamine containing a radiation-polymerizable functional group that is useful as a surface treatment agent, as well as a novel organosilylamine containing a radiation-polymerizable functional group.

As a result of intensive investigation aimed at achieving the above object, the inventors of the present invention developed a method in which, by conducting a desalting reaction of an organosilylamine containing a haloalkyl group and a salt having a radiation-polymerizable functional group, the target organosilylamine could be produced with favorable stability, and they were therefore able to complete the present invention.

In other words, a first aspect of the present invention provides a method of producing an organosilylamine containing a radiation-polymerizable functional group (hereafter also referred to as a "radiation-polymerizable functional group-containing organosilylamine"), the method comprising reacting an organosilylamine containing a haloalkyl group, and at least one salt having a radiation-polymerizable functional group selected from the group consisting of alkali metal salts of organic acids having a radiation-polymerizable functional group and alkaline earth metal salts of organic acids having a radiation-polymerizable functional group, at a temperature within a range from 50 to 150° C.

A second aspect of the present invention provides an organosilylamine containing a radiation-polymerizable functional group, composed of a silazane unit represented by a general formula (1a) shown below:

(1a)

(wherein, $R^1$ represents a (meth)acryloyloxy group, $R^2$ and $R^3$ each represent, independently, a hydrogen atom, an alkyl group of 1 to 10 carbon atoms, or an aryl group of 6 to 10 carbon atoms, and a represents an integer of 0 to 2).

According to the method of producing an organosilylamine of the present invention, because a radiation-polymerizable functional group is introduced from a salt having a radiation-polymerizable functional group into an organosilylamine containing a haloalkyl group, radiation-polymerizable functional group-containing organosilylamines that include novel organosilylamines can be produced stably, with no side reactions between the ammonia or amino groups and the radiation-polymerizable functional group. Furthermore, the salt generated by the desalting reaction can be removed easily by filtration or the like. The produced radiation-polymerizable functional group-containing organosilylamine is useful for introducing radiation-polymerizable functional groups at the terminals or surfaces of inorganic oxides such as silicone or silica, or at the surfaces of inorganic substrates.

DETAILED DESCRIPTION OF THE PREFERRED EMBODIMENTS

A more detailed description of the present invention is presented below. In this description, the term "(meth)acryloyl" (group) is used as a generic term that includes both an acryloyl (group) and a methacryloyl (group), the term "(meth)acrylic acid" is used as a generic term that includes both acrylic acid and methacrylic acid, and the term "(meth)acrylate" is used as a generic term that includes both acrylate and methacrylate.

[Method of Producing Radiation-Polymerizable Functional Group-Containing Organosilylamine]

In the production method of the present invention, a radiation-polymerizable functional group-containing organosilylamine can be produced by conducting a desalting reaction between an organosilylamine containing a haloalkyl group, and at least one salt having a radiation-polymerizable functional group selected from the group consisting of alkali metal salts of organic acids having a radiation-polymerizable functional group and alkaline earth metal salts of organic acids having a radiation-polymerizable functional group.

Radiation-Polymerizable Functional Group-Containing Organosilylamine

There are no particular restrictions on the radiation-polymerizable functional group-containing organosilylamine obtained using the production method of the present invention, provided the organosilylamine contains one or more radiation-polymerizable functional groups within each molecule.

In this description, the term "organosilylamine" is a general description of an organosilicon compound containing a Si—N bond. The term is deemed to include not only organoaminosilanes, but also organosilazanes. The number of amino groups within an organoaminosilane may be any number from 1 to 3. An organosilazane may be either a straight-chain or cyclic structure, and may also include branching.

In the present invention, the term "radiation" includes electromagnetic radiation such as microwaves, infrared radiation, ultraviolet (UV) radiation, X-rays and γ-rays; as well as particle beams such as α-particle beams, proton beams, neutron beams, and electron beams.

Examples of the radiation-polymerizable functional group include an acryloyl group, methacryloyl group, vinyl group or styryl group, and an acryloyl group or methacryloyl group is preferred.

Examples of the radiation-polymerizable functional group-containing organosilylamine produced using the production method of the present invention include organosilylamines composed of a silazane unit represented by a general formula (1) shown below:

(wherein, X represents a straight-chain or branched-chain alkylene group of 1 to 10, preferably 1 to 8, and even more preferably 1 to 5 carbon atoms, $R^1$ represents a (meth)acryloyloxy group, $R^2$ and $R^3$ each represent, independently, a hydrogen atom, an alkyl group of 1 to 10, preferably 1 to 8, and even more preferably 1 to 4 carbon atoms, or an aryl group of 6 to 10, preferably 6 to 8, and even more preferably 6 to 7 carbon atoms, and a represents an integer of 0 to 2).

In those cases where the organosilylamine includes a plurality of silazane units represented by the above general formula (1), the plurality of units may be either the same or different.

Examples of X include alkylene groups such as a methylene group, ethylene group, methylmethylene group, propylene group (trimethylene group or methylethylene group), butylene group (for example, a tetramethylene group, 1,2-butylene group, 1,3-butylene group or 2,3-butylene group), pentene group (for example, a pentamethylene group) or hexene group (for example, a hexamethylene group), and of these, a methylene group or trimethylene group is preferred.

Examples of the groups $R^2$ and $R^3$ include a hydrogen atom; alkyl groups such as a methyl group, ethyl group, propyl group, isopropyl group, butyl group, isobutyl group, sec-butyl group, tert-butyl group, pentyl group, isopentyl group, neopentyl group, hexyl group, heptyl group, 1-ethylpentyl group, octyl group, 2-ethylhexyl group, nonyl group or decyl group; and aryl groups such as a phenyl group, tolyl group, xylyl group or naphthyl group; and of these, a hydrogen atom, methyl group, ethyl group, propyl group, isopropyl group, butyl group or phenyl group is preferred. A methyl group is particularly preferred as $R^2$, and a hydrogen atom is particularly preferred as $R^3$.

Examples of radiation-polymerizable functional group-containing organosilylamines composed of a silazane unit represented by the above general formula (1) include radiation-polymerizable functional group-containing organosilylamines and the like represented by a general formula (1') shown below:

(wherein, X and $R^1$ to $R^3$ are as defined above, and p represents an integer of 0 or greater, typically an integer from 0 to 10, and even more typically an integer from 0 to 5).

Of these compounds, radiation-polymerizable functional group-containing organosilylamines represented by a general formula (2) shown below are preferred.

(2)

(wherein, X, $R^1$ and $R^2$ are as defined above)

Even more preferred examples of radiation-polymerizable functional group-containing organosilylamines composed of a silazane unit represented by the above general formula (1) include the radiation-polymerizable functional group-containing organosilylamines represented by a general formula (3) shown below:

(3)

(wherein, each R represents, independently, a hydrogen atom or a methyl group).

Of the radiation-polymerizable functional group-containing organosilylamines that can be produced using the production method of the present invention, from the viewpoint of ensuring a low boiling point for the nitrogen compounds generated as by-products when the organosilylamine is used as a surface treatment agent or the like, 1,3-bis(acryloyloxymethyl)-1,1,3,3-tetramethyldisilazane, 1,3-bis(methacryloyloxymethyl)-1,1,3,3-tetramethyldisilazane, 1,3-bis(γ-acryloyloxypropyl)-1,1,3,3-tetramethyldisilazane, 1,3-bis(γ-methacryloyloxypropyl)-1,1,3,3-tetramethyldisilazane, acryloyloxymethylmethyltrisilazane, methacryloyloxymethylmethyltrisilazane, acryloyloxymethylmethyltetrasilazane, methacryloyloxymethylmethyltetrasilazane, acryloyloxymethylmethylpolysilazane, methacryloyloxymethylmethylpolysilazane, 3-acryloyloxypropylmethyltrisilazane, 3-methacryloyloxypropylmethyltrisilazane, 3-acryloyloxypropylmethyltetrasilazane, 3-methacryloyloxypropylmethyltetrasilazane, 3-acryloyloxypropylmethylpolysilazane, 3-methacryloyloxypropylmethylpolysilazane, acryloyloxymethylpolysilazane, methacryloyloxymethylpolysilazane, 3-acryloyloxypropylpolysilazane, and 3-methacryloyloxypropylpolysilazane are preferred, and moreover, if the ease of synthesis and identification of the compound is also taken into consideration, then 1,3-bis(acryloyloxymethyl)-1,1,3,3-tetramethyldisilazane, 1,3-bis(methacryloyloxymethyl)-1,1,3,3-tetramethyldisilazane, 1,3-bis(γ-acryloyloxypropyl)-1,1,3,3-tetramethyldisilazane and 1,3-bis(γ-methacryloyloxypropyl)-1,1,3,3-tetramethyldisilazane are particularly preferred.

Organosilylamine Containing a Haloalkyl Group

There are no particular restrictions on the organosilylamine containing a haloalkyl group, provided it contains one or more haloalkyl groups within each molecule that are capable of undergoing a desalting reaction with the above salt having a radiation-polymerizable functional group.

Examples of the haloalkyl group include straight-chain or branched-chain alkyl groups of 1 to 10, preferably 1 to 8, and even more preferably 1 to 5 carbon atoms, that have been substituted with a halogen atom such as a fluorine atom, chlorine atom, bromine atom or iodine atom. Specific examples include a chloromethyl group, 2-chloroethyl group, 3-chloropropyl group, 3-bromopropyl group, 4-chlorobutyl group and 3-chloro-2-methylpropyl group.

In those cases where the target radiation-polymerizable functional group-containing organosilylamine is composed of a silazane unit represented by the general formula (1), the organosilylamine containing a haloalkyl group may be an organosilylamine composed of a silazane unit represented by a general formula (4) shown below:

(4)

(wherein, X, $R^2$, $R^3$ and a are as defined above, and Y represents a halogen atom).

In those cases where this organosilylamine includes a plurality of silazane units represented by the above general formula (4), the plurality of units may be either the same or different.

Examples of Y include a fluorine atom, chlorine atom, bromine atom or iodine atom, although a chlorine atom or bromine atom is preferred.

In those cases where the target radiation-polymerizable functional group-containing organosilylamine is a compound represented by the general formula (1'), an organosilylamine represented by a general formula (4') shown below may be used.

(4')

(wherein, X, Y, $R^1$ to $R^3$, and p are as defined above)

In those cases where the target radiation-polymerizable functional group-containing organosilylamine is a compound represented by the general formula (2), an organosilylamine represented by a general formula (5) shown below may be used.

(5)

(wherein, X, Y and $R^2$ are as defined above)

In those cases where the target radiation-polymerizable functional group-containing organosilylamine is a compound represented by the general formula (3), an organosilylamine represented by a general formula (6) shown below may be used.

(6)

(wherein, Y is as defined above)

Specific examples of the organosilylamine containing a haloalkyl group include 1,3-bis(chloromethyl)-1,1,3,3-tetramethyldisilazane, 1,3-bis(γ-chloropropyl)-1,1,3,3-tetramethyldisilazane, chloromethylmethyltrisilazane, chloromethylmethyltetrasilazane, chloromethylmethylpolysilazane, 3-chloropropylmethyltrisilazane, 3-chloropropylmethyltetrasilazane, 3-chloropropylmethylpolysilazane, chloromethylpolysilazane and 3-chloropropylpolysilazane, and this compound may be selected in accordance with the target radiation-polymerizable functional group-containing organosilylamine.

Salt Having Radiation-Polymerizable Functional Group

The salt having a radiation-polymerizable functional group is at least one salt selected from the group consisting of alkali metal salts of organic acids having a radiation-polymerizable functional group and alkaline earth metal salts of organic acids having a radiation-polymerizable functional group. Examples of organic acids having a radiation-polymerizable functional group include acrylic acid and methacrylic acid. Examples of the alkali metal include lithium, sodium and potassium, and sodium and potassium are preferred. Examples of the alkaline earth metal include calcium, strontium and barium, and calcium is preferred.

Examples of the salt having a radiation-polymerizable functional group include (meth)acrylate salts represented by a general formula (7) shown below:

(7)

(wherein, $R^1$ is as defined above, and M represents an alkali metal atom or an alkaline earth metal atom), namely, alkali metal salts and alkaline earth metal salts of (meth)acrylic acid. Specific examples of the (meth)acrylate salts represented by the above general formula (7) include potassium acrylate, potassium methacrylate, sodium acrylate, sodium methacrylate, lithium acrylate and lithium methacrylate, and of these, from the viewpoint of reactivity, potassium acrylate, potassium methacrylate, sodium acrylate and sodium methacrylate are preferred, and potassium acrylate and potassium methacrylate are particularly desirable.

Reaction Conditions

During synthesis of the radiation-polymerizable functional group-containing organosilylamine of the present invention, the desalting reaction is preferably conducted under heating and within an organic solvent in order to accelerate the reaction speed.

The organic solvent is preferably an organic solvent that contains no active hydrogen atoms, and of such solvents, polar organic solvents are particularly preferred. Specific examples of the organic solvent include saturated hydrocarbon-based solvents such as hexane and decane; polyether-based solvents such as triethylene glycol dimethyl ether; aromatic solvents such as benzene and toluene; ketone-based solvents such as acetone, methyl ethyl ketone, and methyl isobutyl ketone; and amide-based solvents such as formamide and dimethylformamide. Of the above organic solvents, from the viewpoints of the degree of polarity and the boiling point, dimethylformamide and toluene are particularly preferred. The organic solvent may be either a single solvent, or a combination of two or more different solvents.

The reaction temperature must be set within a range from 50 to 150° C., and is preferably within a range from 100 to 130° C. If the temperature is lower than 50° C., then the desalting reaction may not proceed satisfactorily, whereas if the temperature exceeds 150° C., there is a chance that the produced radiation-polymerizable functional group-containing silazane may polymerize.

When conducting the reaction of the present invention, a polymerization inhibitor is preferably used to stabilize the produced radiation-polymerizable functional group-containing organosilylamine. The polymerization inhibitor may be any of the generally available inhibitors, although of these, a hindered phenol-based compound is particularly preferred. The quantity added may be similar to the quantity added in typical applications that employ a polymerization inhibitor, and for example, a quantity within a range from 0.001 to 1.0% by mass relative to the mass of the radiation-polymerizable functional group-containing organosilylamine is preferred.

Purification Method

The alkali metal halide or alkaline earth metal halide produced in the above desalting reaction can be separated from the target radiation-polymerizable functional group-containing organosilylamine by a conventional technique known to those skilled in the art, such as filtration or the like. The radiation-polymerizable functional group-containing organosilylamine may also be further purified using other conventional techniques known to those skilled in the art, including distillation under reduced pressure or liquid column chromatography or the like.

Raw Materials and Product Combinations

An organosilylamine composed of a silazane unit represented by the above general formula (1) can be produced, for example, by conducting a desalting reaction within an organic solvent between an organosilylamine composed of a silazane unit represented by the above general formula (4) and a (meth)acrylate salt represented by the above general formula (7).

Furthermore, an organosilylamine represented by the above general formula (2) can be produced, for example, by conducting a desalting reaction within an organic solvent between an organosilylamine represented by the above general formula (5) and a (meth)acrylate salt represented by the above general formula (7).

Moreover, an organosilylamine represented by the above general formula (3) can be produced, for example, by conducting a desalting reaction within an organic solvent between an organosilylamine represented by the above general formula (6) and a (meth)acrylate salt represented by the above general formula (7).

[Radiation-Polymerizable Functional Group-Containing Organosilylamine]

A radiation-polymerizable functional group-containing organosilylamine of the present invention is a radiation-polymerizable functional group-containing organosilylamine composed of a silazane unit represented by a general formula (1a) shown below:

(wherein, $R^1$ to $R^3$ and a are as defined above).

Examples of the radiation-polymerizable functional group-containing organosilylamine composed of a silazane unit represented by the above general formula (1a) include radiation-polymerizable functional group-containing organosilylamines represented by a general formula (1a') shown below:

(wherein, $R^1$ to $R^3$ and p are as defined above), and of these compounds, radiation-polymerizable functional group-containing organosilylamines represented by a general formula (2a) shown below are preferred, (wherein, $R^1$ and $R^2$ are as defined above), and radiation-polymerizable functional group-containing organosilylamines represented by the above general formula (3) are particularly desirable. The radiation-polymerizable functional group-containing organosilylamine of the present invention can be obtained using the production method of the present invention.

EXAMPLES

A more detailed description of the present invention is provided below, based on a series of examples and comparative examples, although the present invention is in no way restricted by the examples presented below. In the examples, GC is an abbreviation for gas chromatography, NMR is an abbreviation for nuclear magnetic resonance spectroscopy, and IR is an abbreviation for infrared spectroscopy.

Example 1

Figure 1:
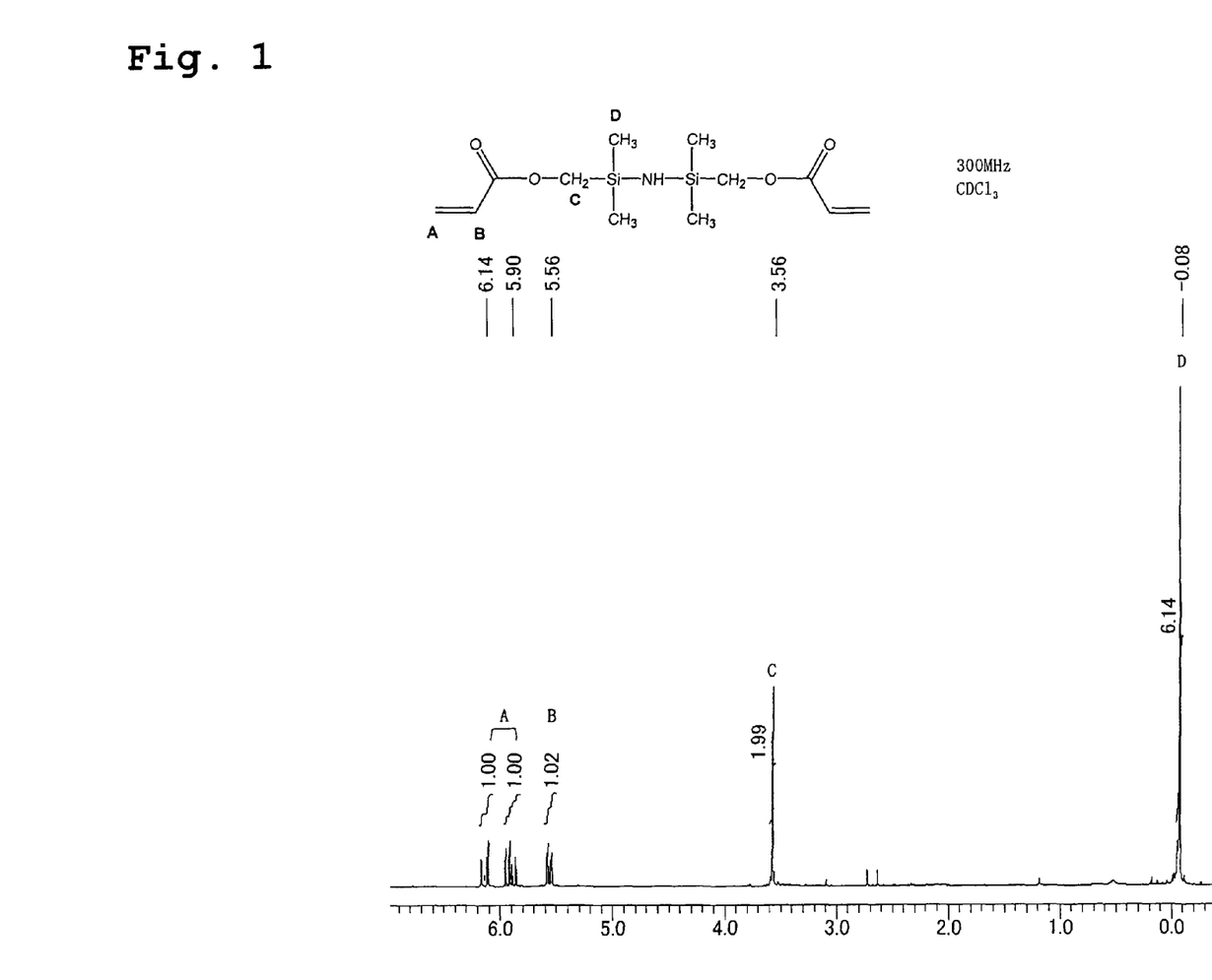
FIG. 1 is a diagram showing the $^1$H NMR spectrum of the reaction product from Example 1.
Figure 2:
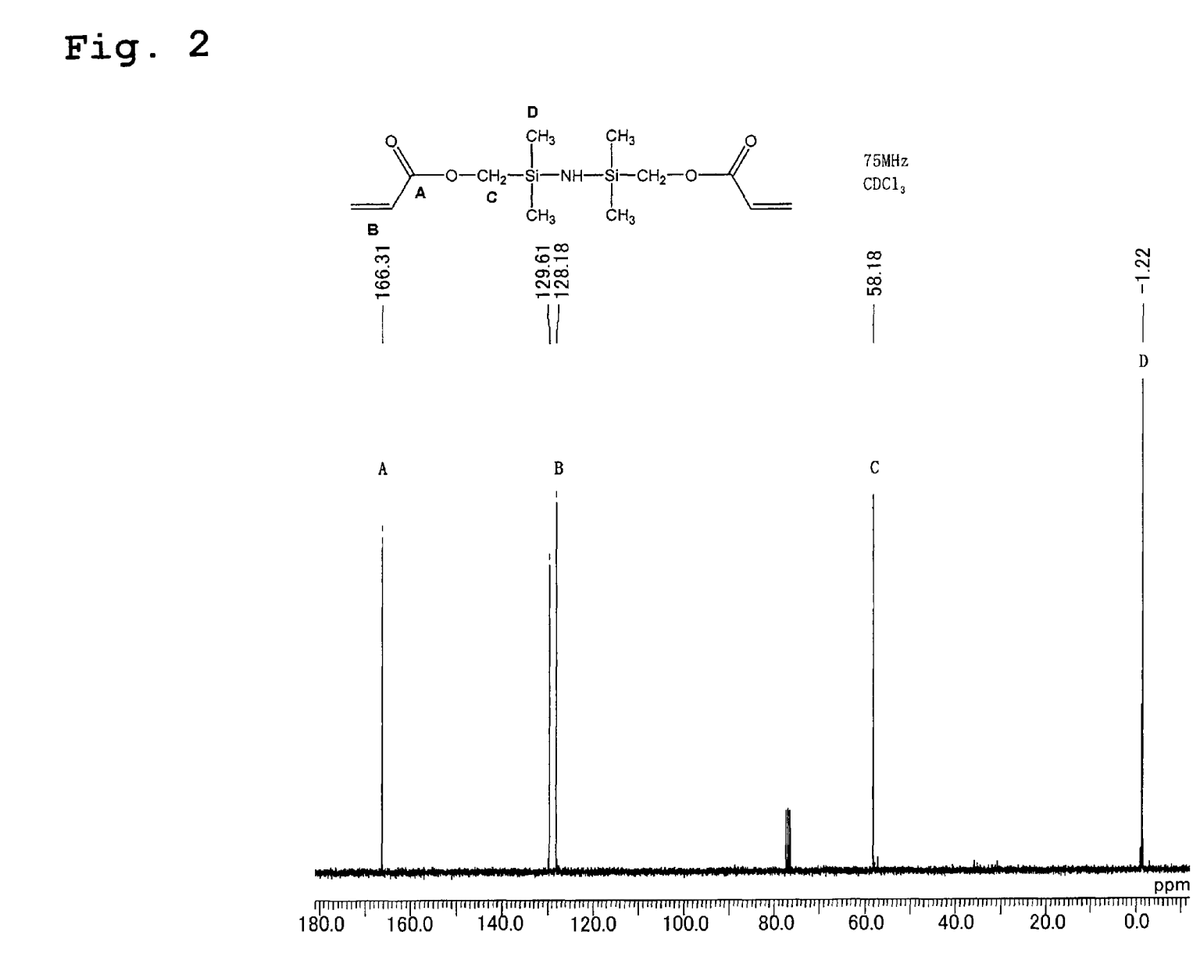
FIG. 2 is a diagram showing the $^{13}$C NMR spectrum of the reaction product from Example 1.
Figure 3:
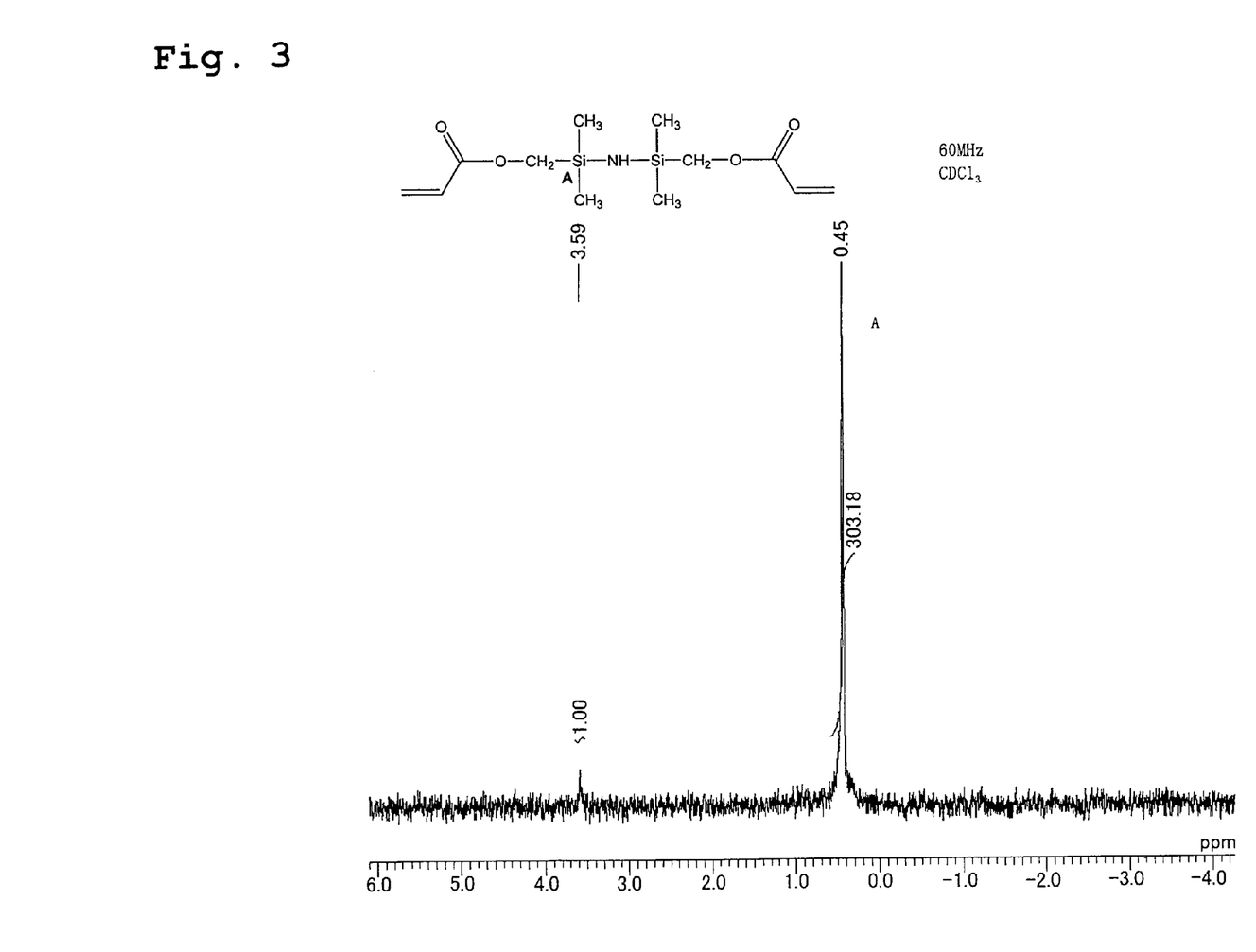
FIG. 3 is a diagram showing the $^{29}$Si NMR spectrum of the reaction product from Example 1.
Figure 4:
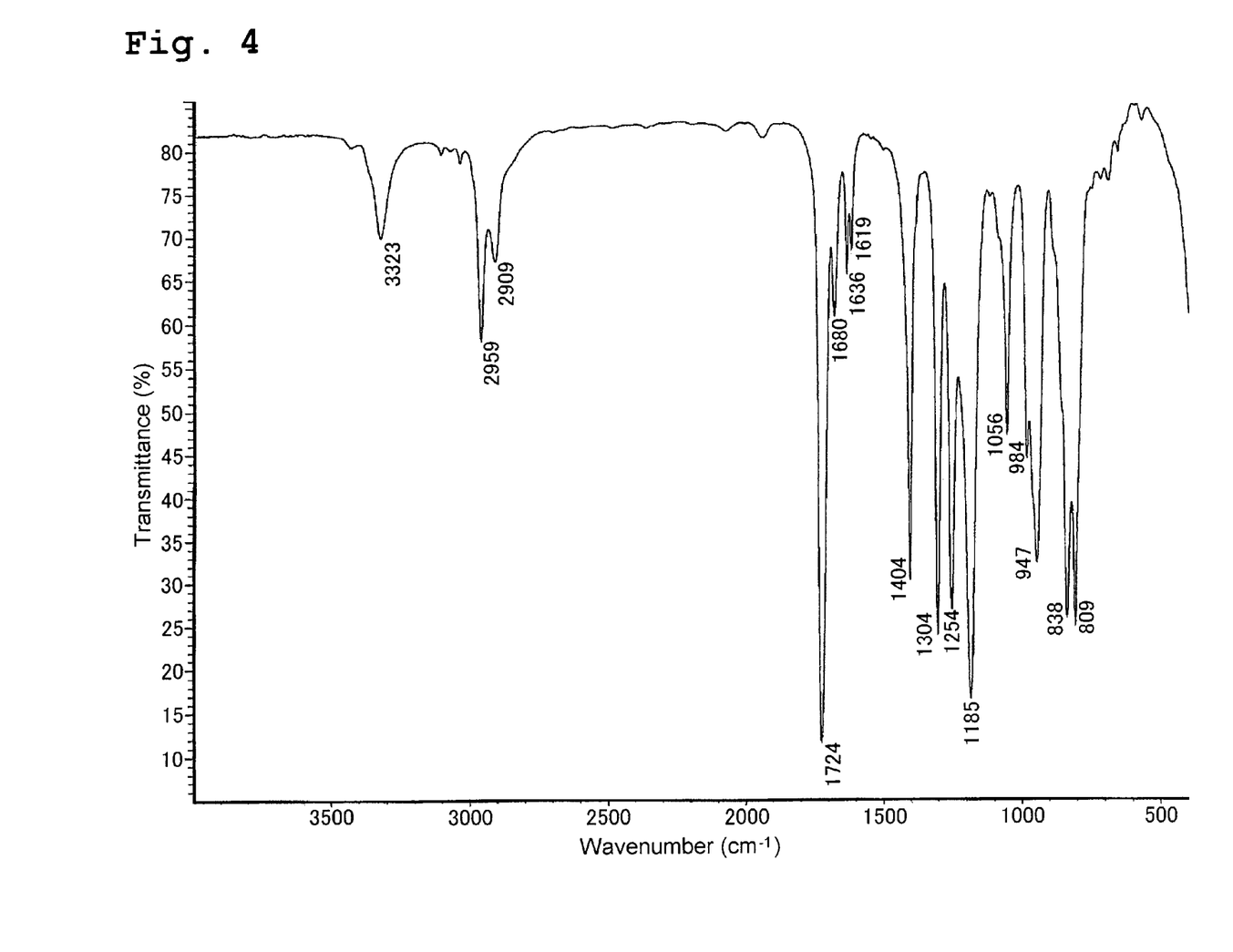
FIG. 4 is a diagram showing the IR spectrum of the reaction product from Example 1.

220 g (2.0 mols) of potassium acrylate, 200 g of dimethylformamide, 200 g of toluene, and 2.7 g of bis-t-butylhydroxytoluene were placed in a 1 liter glass separable flask fitted with a thermometer, a water-cooled condenser and a dropping funnel, the mixture was heated to 140° C., and any moisture contained within the toluene and the potassium acrylate was distilled and removed from the reaction system. Subsequently, the temperature was lowered to 120° C., and 230 g (1 mol) of 1,3-bis(chloromethyl)-1,1,3,3-tetramethyl-disilazane was added dropwise to the reaction system. The reaction mixture was then heated under reflux at 120° C., with constant stirring, while the progress of the reaction was tracked by GC. After 3 hours, the peak attributable to the raw material silazane had completely disappeared, and the appearance of a new peak attributable to the reaction product was confirmed by GC, indicating the end point of the reaction. Subsequently, the produced potassium chloride was removed by filtration, and the reaction solvent was removed under reduced pressure, yielding a light yellow liquid. GC revealed that the purity of this reaction product was at least 97%. Furthermore, analysis using $^1$H NMR, $^{13}$C NMR, $^{29}$Si NMR and IR spectroscopy confirmed that the reaction product was the target compound, namely 1,3-bis(acryloyloxymethyl)-1,1,3,3-tetramethyldisilazane. The NMR spectra of this compound are shown in FIG. 1 to FIG. 3, and the IR spectrum is shown in FIG. 4.

Example 2

With the exception of replacing the 220 g (2.0 mols) of potassium acrylate from Example 1 with 248 g (2.0 mols) of potassium methacrylate, a light yellow liquid was obtained in the same manner as Example 1. GC revealed that the purity of this reaction product was at least 97%. Furthermore, analysis using $^1$H NMR, $^{13}$C NMR, $^{29}$Si NMR and IR spectroscopy confirmed that the reaction product was the target compound, namely 1,3-bis(methacryloyloxymethyl)-1,1,3,3-tetramethyldisilazane.

$^1$H NMR (300 MHz, CDCl$_3$, δ): −0.08 ppm (s, 12H), 1.72 ppm (s, 6H), 3.57 ppm (s, 4H), 5.31 ppm (m, 2H), 5.86 ppm (m, 2H)

$^{29}$Si NMR (60 MHz, CDCl$_3$, δ): 0.5 ppm

Example 3

With the exception of replacing the 230 g (1 mol) of 1,3-bis(chloromethyl)-1,1,3,3-tetramethyldisilazane from Example 1 with 286 g (1 mol) of 1,3-bis(γ-chloropropyl)-1,1,3,3-tetramethyldisilazane, a light yellow liquid was obtained in the same manner as Example 1. GC revealed that the purity of this reaction product was at least 97%. Furthermore, analysis using $^1$H NMR, $^{13}$C NMR, $^{29}$Si NMR and IR spectroscopy confirmed that the reaction product was the target compound, namely 1,3-bis(γ-acryloyloxypropyl)-1,1,3,3-tetramethyldisilazane.

$^1$H NMR (300 MHz, CDCl$_3$, δ): −0.08 ppm (s, 12H), 0.36 ppm (t, J=7 Hz, 4H), 1.46 ppm (quint, J=7 Hz, 4H), 3.81 ppm (t, J=7 Hz, 4H), 5.58 ppm (m, 2H), 5.92 ppm (m, 2H), 6.13 ppm (m, 2H)

$^{29}$Si NMR (60 MHz, CDCl$_3$, δ): 0.5 ppm

Example 4

With the exceptions of replacing the 220 g (2.0 mols) of potassium acrylate from Example 1 with 248 g (2.0 mols) of potassium methacrylate, and replacing the 230 g (1 mol) of 1,3-bis(chloromethyl)-1,1,3,3-tetramethyldisilazane from Example 1 with 286 g (1 mol) of 1,3-bis(γ-chloropropyl)-1,1,3,3-tetramethyldisilazane, a light yellow liquid was obtained in the same manner as Example 1. GC revealed that the purity of this reaction product was at least 97%. Furthermore, analysis using $^1$H NMR, $^{13}$C NMR, $^{29}$Si NMR and IR spectroscopy confirmed that the reaction product was the target compound, namely 1,3-bis(γ-methacryloyloxypropyl)-1,1,3,3-tetramethyldisilazane.

$^1$H NMR (300 MHz, CDCl$_3$, δ): −0.07 ppm (s, 12H), 0.38 ppm (t, J=7 Hz, 4H), 1.46 ppm (quint, J=7 Hz, 4H), 1.75 ppm (s, 6H), 3.80 ppm (t, J=7 Hz, 4H), 5.35 ppm (m, 2H), 5.79 ppm (m, 2H)

$^{29}$Si NMR (60 MHz, CDCl$_3$, δ): 0.5 ppm

Comparative Example 1

With the exception of lowering the temperature from the 120° C. used in Example 1 to 40° C., the same procedure as Example 1 was performed up until the operation of adding the 230 g (1 mol) of 1,3-bis(chloromethyl)-1,1,3,3-tetramethyldisilazane dropwise to the reaction system. Subsequently, the reaction mixture was heated at 40° C. for 3 hours under constant stirring while the progress of the reaction was tracked by GC, but only the peak attributable to the raw material silazane was detected, and the reaction did not proceed at all.

Comparative Example 2

With the exceptions of not lowering the temperature to 120° C. as in Example 1, but rather raising the temperature to 160° C., and then conducting the reaction at a reflux temperature of 160° C. instead of 120° C., a reaction was performed in the same manner as Example 1. However, the reaction system gradually thickened, and eventually formed a gel, making subsequent handling impossible.

What is claimed is:

1. A method of producing an organosilylamine containing a radiation-polymerizable functional group, the method comprising reacting, in the absence of a catalyst, an organosilylamine containing a haloalkyl group, and at least one salt having a radiation-polymerizable functional group selected from the group consisting of alkali metal salts of organic acids having a radiation-polymerizable functional group and alkaline earth metal salts of organic acids having a radiation-polymerizable functional group, at a temperature within a range from 50 to 150° C.

2. The method according to claim 1, wherein the organosilylamine containing a haloalkyl group is an organosilylamine composed of a silazane unit represented by a general formula (4) shown below:

(wherein, X represents a straight-chain or branched-chain alkylene group of 1 to 10 carbon atoms, R$^2$ and R$^3$ each represent, independently, a hydrogen atom, an alkyl group of 1 to 10 carbon atoms, or an aryl group of 6 to 10 carbon atoms, a represents an integer of 0 to 2, and Y represents a halogen atom), the salt having a radiation-polymerizable functional group is a (meth)acrylate salt represented by a general formula (7) shown below:

R$^1$–M     (7)

(wherein, R$^1$ represents a (meth)acryloyloxy group, and M represents an alkali metal atom or an alkaline earth metal atom), and a produced organosilylamine containing a radiation-polymerizable functional group is an organosilylamine composed of a silazane unit represented by a general formula (1) shown below:

(wherein, X, R$^1$ to R$^3$ and a are as defined above).

3. The method according to claim 2, wherein the organosilylamine composed of a silazane unit represented by the general formula (4) is an organosilylamine represented by a general formula (5) shown below:

(wherein, X, Y and R$^2$ are as defined above), and the organosilylamine composed of a silazane unit represented by the general formula (1) is an organosilylamine represented by a general formula (2) shown below:

(wherein, X, R$^1$ and R$^2$ are as defined above).

4. The method according to claim 3, wherein the organosilylamine represented by the general formula (5) is an organosilylamine represented by a general formula (6) shown below:

(wherein, Y is as defined above), and the organosilylamine represented by the general formula (2) is an organosilylamine represented by a general formula (3) shown below:

(wherein, each R represents, independently, a hydrogen atom or a methyl group).

5. The method according to claim 1, wherein the salt having a radiation-polymerizable functional group is an alkali metal salt of an organic acid having a radiation-polymerizable functional group, and the alkali metal salt is at least one salt selected from the group consisting of sodium methacrylate, potassium methacrylate, sodium acrylate and potassium acrylate.

6. The method according to claim 1, wherein reaction is conducted within an organic solvent.

7. The method according to claim 1, further comprising, prior to the reacting step, preparing a mixture consisting of the organosilylamine and the at least one salt.

8. The method according to claim 1, further comprising, prior to the reacting step, preparing a mixture consisting of the organosilylamine, the at least one salt, and an organic solvent.

9. The method according to claim 1, further comprising, prior to the reacting step, preparing a mixture consisting of the organosilylamine, the at least one salt, and a polymerization inhibitor.

10. The method according to claim 1, further comprising, prior to the reacting step, preparing a mixture consisting of the organosilylamine, the at least one salt, an organic solvent, and a polymerization inhibitor.

11. The method according to claim 6, wherein the organic solvent is a polar organic solvent.

* * * * *